United States Patent [19]

Leplat-Gryspeerdt

[11] 4,106,908

[45] Aug. 15, 1978

[54] METHOD FOR THE DETERMINATION OF THE ORGANIC CARBON CONTENT IN MINERAL-CONTAINING MATERIALS

[75] Inventor: Paul A. Leplat-Gryspeerdt, Louvain, Belgium

[73] Assignee: Labofina S.A., Brussels, Belgium

[21] Appl. No.: 786,851

[22] Filed: Apr. 12, 1977

[51] Int. Cl.² .................. G01N 31/08; G01N 31/12; G01N 33/24
[52] U.S. Cl. ..................... 23/230 PC; 23/230 EP; 23/232 C; 23/253 PC
[58] Field of Search ...... 23/230 PC, 253 PC, 230 EP, 23/232 R, 254 R, 232 C

[56] References Cited

U.S. PATENT DOCUMENTS

| 2,437,045 | 3/1948 | Roper | 23/232 R |
|---|---|---|---|
| 2,854,396 | 9/1958 | Hunt et al. | 23/230 EP X |
| 3,168,378 | 2/1965 | Maresh et al. | 23/230 PC |
| 3,304,159 | 2/1967 | Hinsvark | 23/230 PC |
| 3,698,869 | 10/1972 | Condon | 23/230 PC X |
| 3,811,838 | 5/1974 | Saito et al. | 23/230 PC |
| 3,861,874 | 1/1975 | Krc | 23/230 PC |
| 3,880,587 | 4/1975 | Syakasits et al. | 23/230 PC |
| 3,953,171 | 4/1976 | Espitabe et al. | 23/230 PC X |

Primary Examiner—Joseph Scovronek

[57] ABSTRACT

A method for the determination of the organic carbon content of raw mineral materials, e.g., raw rocks, sediments and the like, is disclosed which comprises pyrolyzing a sample of raw material which is previously crushed at a temperature of between 400° and 1,000° C, analyzing the pyrolysis gases by gas chromatography, and determining the benzene content of the pyrolysis gases. By determining the benzene content of pyrolysis products from raw materials with a known organic carbon content, the relationship between these two values at a given pyrolysis temperature is determined prior to the analysis of unknown material. An apparatus for effecting this determination method is also disclosed.

6 Claims, 3 Drawing Figures

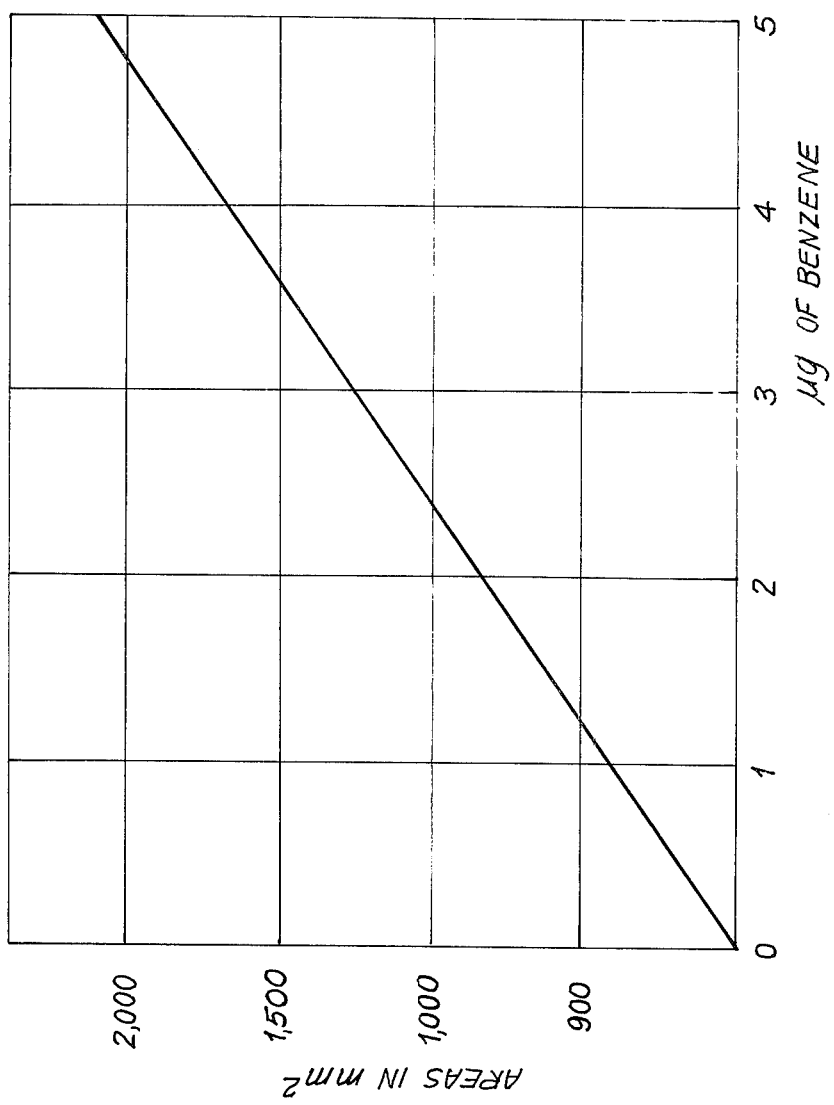
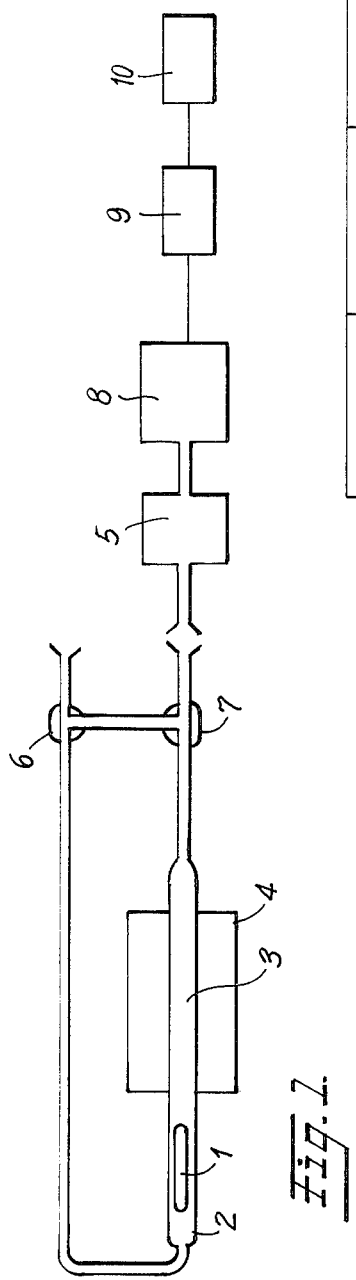

METHOD FOR THE DETERMINATION OF THE ORGANIC CARBON CONTENT IN MINERAL-CONTAINING MATERIALS

BACKGROUND OF THE INVENTION

The present invention relates to a method for determining the organic carbon content of raw mineral materials, e.g., crushed raw rocks and the like. The present invention is more particularly concerned with a method for determining in a short period of time the organic carbon content by using a small amount sample of the raw material and to an apparatus for performing such a determination.

The determination of the organic carbon content in mineral materials has a wide field of practical applications. It is very convenient to evaluate the geological sediments from samples which may be carried on the surface of the ground, in a drilling well, on drill cuttings or on drilling cores.

One of the most important geochemical parameters to evaluate for an oil drilling certainly is the amount of available organic matter, including both soluble and insoluble organic components. The organic carbon content of a kerogen rock, which represents the insoluble organic matter closely associated to this rock, should advantageously be determined and made visible with a diagraph on the very site of an oil drilling.

Up to now, the organic carbon content has always been determined according to a very time consuming method which requires previous physico-chemical treatment of the sediments, and especially an extraction by a solvent and an acid treatment to eliminate the carbonates. The sample is then submitted to a pyrolysis in the presence of a catalyst and the amount of $CO_2$ which is formed from the organic matter is determined. It is obvious that with such a method, the carbonates present in the rock must be completely eliminated, because they also emit some $CO_2$ which is not representative of the organic carbon content of the rock. The time which is needed for these various operations is at least one day, and the advantage of a method allowing determination of the organic carbon content in a short period of time is easily understood.

A method for determining the carbonic gas content of geological sediments, which have not been submitted to any physico-chemical treatments, has already been proposed. This method comprises carrying out the pyrolysis of the sediments within narrowly defined temperature limits, namely between 150° and 400° C. This determination method for the carbonic gas in untreated samples is not suitable to determine the organic carbon content. It only gives indications on the state of diagenesis of the matter, because the determination of the carbonic gas emitted does not allow to establish a correlation with the organic total carbon content of the matter.

SUMMARY OF THE INVENTION

It is an object of the present invention to provide a process for the determination of the organic carbon content of raw mineral material, especially raw rock material.

It is an object of the present invention to provide such a process which allows determination from small samples of the raw material, e.g., in the range of several milligrams. It is a further object of the present invention to provide such a process which permits determination in a short period of time, e.g., within about 10 minutes.

It is a further object of the present invention to provide such a process which permits determination without any prior physico-chemical treatment of the sample, except for crushing any rocky material.

It is a further object of the present invention to provide such a process which can be effected in the presence of inorganic carbonates.

It is still a further object of the present invention to provide an apparatus for effecting such a process.

In order to accomplish the foregoing objects according to the present invention, there is provided a method for determining the organic carbon content of raw mineral materials which comprises the steps of:

(a) determining the relationship between the percent by weight, amount of organic carbon content of raw mineral materials, and the ppm amount of benzene present in the pyrolysis gases which are formed in a pyrolysis apparatus upon pyrolysis of samples of raw mineral materials of known organic carbon content at a pyrolysis temperature of between about 400° and about 1,000° C under an inert gas atmosphere, (b) introducing a weighed sample of a crushed raw mineral material of unknown organic carbon content into said pyrolysis apparatus, (c) pyrolyzing the sample under an inert gas atmosphere at the same temperature as that which is used in the determining step (a) whereby pyrolysis gases are formed, (d) determining the ppm amount of benzene which is present in the pyrolysis gases, and (e) determining the percent per weight amount of organic carbon content in the crushed raw mineral material which is equivalent to said ppm amount of benzene determined in step (d) by comparing to the relationship which has been determined in step (a).

It has been found that by pyrolyzing raw mineral material, such as rocks, sediments and the like, having an organic carbon content in an inert gas atmosphere at temperatures between 400° and 1,000° C, pyrolysis gases are formed which contain an amount of benzene which is a linear function of the amount of the organic carbon content of the raw mineral.

According to the present invention, there is further provided an apparatus for determining the organic carbon content of raw mineral materials comprising:

(a) a pyrolyzing unit comprising a stand-by zone for inserting a sample holder and connected thereto a pyrolyzing zone provided with a heating means, a gas inlet provided with a three-way valve connected to the stand-by zone for introducing a carrier gas, a gas outlet provided with a three-way valve connected to the pyrolyzing zone and a tube directly connecting the gas inlet and the gas outlet for passing a carrier gas from the gas inlet to the gas outlet without passing it through the stand-by zone and the pyrolyzing zone;

(b) a gas chromatography column connected to the gas outlet of the pyrolyzing unit; and, (c) a detector connected to the gas chromatography column.

Further objects, features and advantages of the present invention will become apparent from the detailed description of the invention and its preferred embodiments which follow when considered together with the accompanying figures of drawing.

BRIEF DESCRIPTION OF THE DRAWINGS

FIG. 1 is a schematic view of the apparatus according to the invention;

FIG. 3 is a graph showing the relationship between the amount of benzene and the area of the peak corresponding to benzene in the chromatogram.

DETAILED DESCRIPTION OF THE INVENTION

Figure 2:
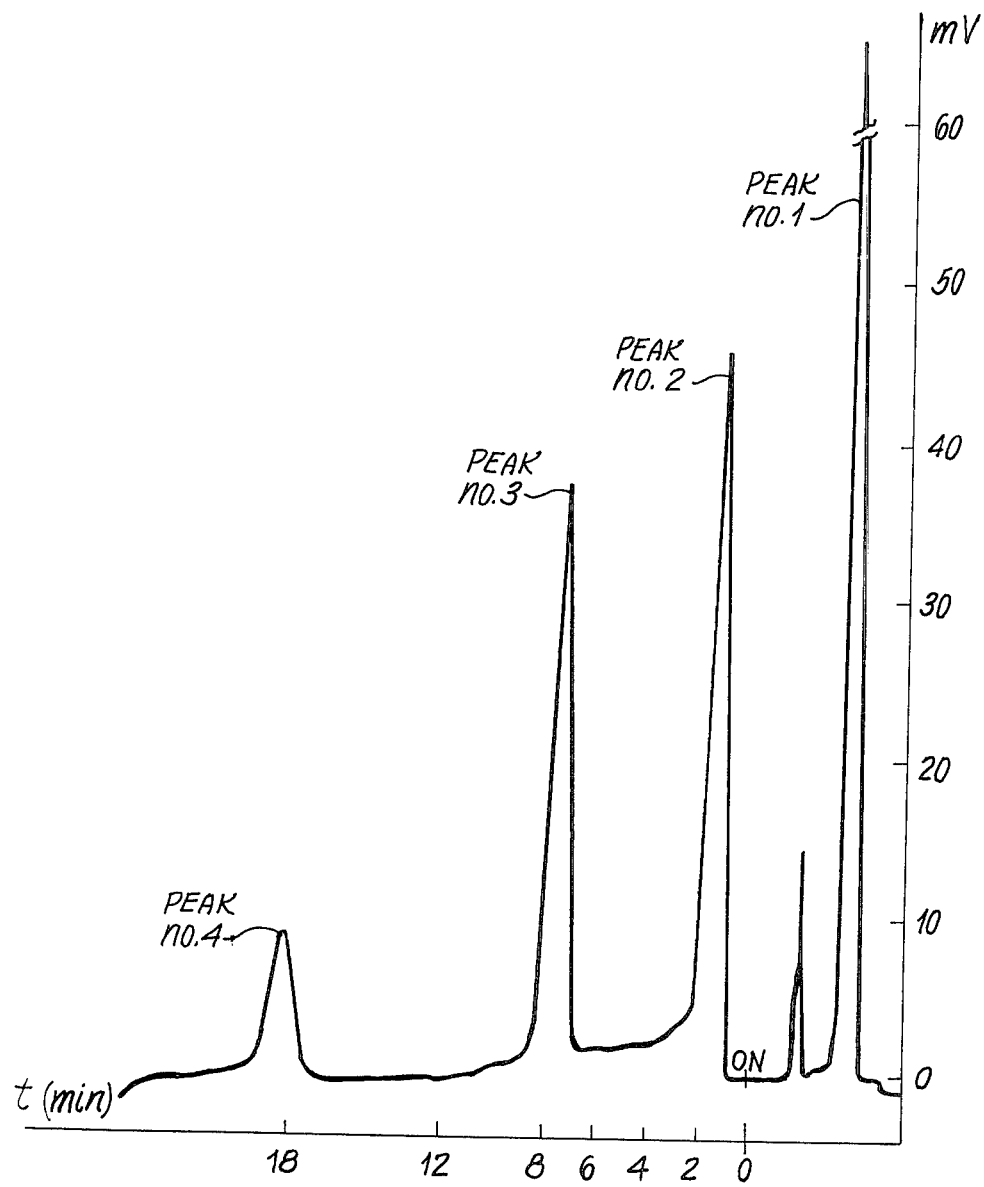
FIG. 2 is a chromatogram of the pyrolysis products of a raw rock material.

The method of the present invention for determining the organic carbon content of raw mineral materials, such as rocks, sediments and the like, comprises weighing a sample of the raw mineral material which is previously crushed, sweeping a pyrolysis furnace with an inert gas, introducing the sample into this pyrolysis furnace, pyrolyzing the sample under an inert atmosphere at a temperature comprised between 400° and 1,000° C, thereafter sweeping the pyrolysis furnace with an inert gas in order to carry the pyrolysis products to a chromatography column, determining with this column the benzene content of the pyrolysis products, and determining the organic carbon content of the mineral material which is equivalent to this amount of benzene according to the relationship between the organic carbon content of the raw mineral material expressed in percent by weight and the benzene content of the pyrolysis gases expressed in ppm, which has been previously determined for the same apparatus and the same temperature.

One of the advantages of the present invention resides in the fact that the sample of raw material which is to be analyzed does not have to be previously submitted to any physico-chemical treatment, except crushing. The considerable loss of time due to previous treatments which are necessary with the other methods is thus avoided. Moreover, the presence of any carbonates does not interfere with the determination of the benzene content. Carbonates had to be completely eliminated in the prior art processes for the determination of the organic carbon content. Furthermore, the determination of benzene, for instance by pyrochromatography, may be carried out on the very site of a drilling. Each determination does not require more than about ten minutes. Therefore, a graphical representation can readily be prepared which, for instance, shows the evolution of the per weight percentage of the organic carbon content in different sediments as a function of the depth of the drilling.

On the other hand, this method can be applied to various raw materials and therefore has a wide field of applications. The most various raw materials, such as samples of soil, recent sediments, non-sedimentary rocks, agglomerates and the like, may be analyzed by this method. Therefore, the method of the present invention may be applied to surface prospecting for petroleum or mining purposes, or for other purposes, as for instance, pollution detection.

The apparatus which is used comprises a pyrolysis furnace connected to a gas chromatography column. The temperature of the pyrolysis furnace is generally comprised between 400° and 1,000° C. The pyrolysis is carried out under an atmosphere of inert gas, such as argon, helium, nitrogen, etc. It may be carried out on any sample of raw materials.

The method of the present invention particularly allows determination of the organic carbon content of raw geological sediments within relatively wide limits. It is preferably applied when this content is between about 0.2% and about 50%. Rocks or sediments, the organic carbon content of which is outside of these limits, present only little interest with regard to the petroleum industry.

The linear relationship between the benzene content of the pyrolysis products and the organic carbon content of the pyrolyzed material is determined from the results of analysis of several hundreds of samples, e.g., between about 100 and about 300 samples, for each of which the benzene content has been determined after pyrolysis, and the carbon content has been determined by a conventional method. This relationship is a linear function which is represented by the equation $y = ax + b$. The coefficients $a$ and $b$ not only depend on the number of tested samples, but also on the apparatus and on the pyrolysis temperature.

The determination of this relationship and the further embodiments of the present invention will now be described in the following examples, which further illustrate the present invention, but without limiting it, with reference to the accompanying drawings.

EXAMPLE 1

The determination of the carbon content of a raw material is effected in an apparatus according to FIG. 1 as follows.

The previously crushed raw sample is weighed in a sample holder 1 which may be a boat or a tube made of quartz or stainless steel. The sample is thereafter set in a stand-by place 2 which is purged with an inert carrier gas. As an inert gas, there may be cited argon, helium, nitrogen, etc.

The stand-by place 2 extends into a tube 3 which can be heated to a temperature of between 400° and 1,000° C with a conventional heating device 4. This tube 3 constitutes the pyrolysis furnace 3.

In the circuit of the carrier gas, before the stand-by place 2 and just at the entrance of the chromatograph 5, two electromagnetically controlled three-way valves 6 and 7, which can be opened in three directions are inserted. These valves 6 and 7 allow to pass the carrier gas either through the stand-by place 2 and the pyrolysis furnace 3 and then through the chromatography column 5 and the detector 8, or directly through the chromatography column 5 and the detector 8.

A conventional column for the separation of $C_6$ hydrocarbons, for instance benzene, and other aromatic hydrocarbons, such as toluene and xylene, may be used as chromatography column 5.

The detector 8 which is connected to the chromatography column 5 is a flame ionization detector. This device is connected to either a recording device 9 or an integrating device 10 or both. These devices provide diagrams from which the amounts of the various components of the pyrolysis gases can be seen.

In the diagram which is shown in FIG. 2, the peak No. 1 represents the air which is chromatographed while the apparatus is purged, the peak No. 2 represents the light hydrocarbons, the peak No. 3 represents the benzene, and the peak No. 4 represents the toluene. Any other device detecting benzene may also be used, such as, for instance, an infra-red detector.

(A) with this apparatus, first the linear relationship between the organic carbon content of raw rock sediments and the benzene content of the pyrolysis products which are obtained from these rocks is determined by treating 195 samples. These 195 samples are pyrolyzed at a temperature of 600° C (according to the hereinabove described embodiment) and the benzene content of the products of each pyrolysis is determined. According to a known process, the organic carbon content of these samples is determined. From the analysis of the results it is found that the relationship is a linear function which is expressed by the following equation:

$$y = 18.8\ x - 0.32$$

wherein $y$ represents the benzene content expressed in ppm, and $x$ the organic carbon content, expressed in percent by weight.

(B) On the basis of this relationship, the organic carbon content of any sample of raw material, for instance, raw rock, material is determined in a very short period of time.

In this way, the sample of raw rock is previously crushed in order to obtain particles of a mean size of 0.25 mm. Thereafter 20 mg of each sample are weighed in a stainless steel tube 1. The charged tube is then introduced into the stand-by place 2 of the pyrolysis furnace. The stand-by place is purged with nitrogen as a carrier gas for 30 seconds. The outcoming gases, e.g., the air, are chromatographed and are represented by peak No. 1 of FIG. 2. The pyrolysis furnace is maintained under nitrogen atmosphere, but at the same time disconnected from the carrier gas circuit by means of the electromagnetic valves (6 and 7) which are positioned in such a way that the inert vehicular gas is passed directly to the chromatography column. Thereafter, by means of shaking the apparatus, the sample-holder tube is passed on into the pyrolysis furnace 3 which is heated at 600° C. The pyrolysis time is 5 minutes. The position of the electromagnetic valves (6 and 7) is then changed in order to again include the pyrolysis furnace in the inert carrier gas circuit. The nitrogen flow then carries the pyrolysis products to the chromatography column 5 and the flame ionization detector 8.

The diagrams corresponding to the various compounds are recorded, and among them, peak No. 3 of FIG. 2 is identified as representing benzene. This peak area is then measured.

By means of the reference curve shown in FIG. 3, the benzene content was determined from the peak area. The reference curve shown in FIG. 3 has been established from benzene standard solutions which have been pyrolyzed at 600° C. This curve shows the relationship between the amount of benzene and the area which is covered by the peak of the chromatogram, which corresponds to the benzene.

By way of control, the organic carbon content of the samples is determined according to a known process.

The results obtained with samples of various raw rocks are indicated in the hereinbelow Table I.

TABLE I

| Sample | Benzene content (ppm) of the pyrolysis products | Organic carbon content of the raw material according to the relationship $y = 18.8\ x - 0.32$ (*) (% by weight) | Organic carbon content of the raw material according to a known process (% by weight) |
|---|---|---|---|
| 1 | 4.2 | 0.2 | 0.24 |
| 2 | 40.2 | 2.00 | 2.16 |
| 3 | 98.5 | 5.00 | 5.26 |
| 4 | 367.0 | 20.00 | 19.54 |

TABLE I-continued

| Sample | Benzene content (ppm) of the pyrolysis products | Organic carbon content of the raw material according to the relationship $y = 18.8\ x - 0.32$ (*) (% by weight) | Organic carbon content of the raw material according to a known process (% by weight) |
|---|---|---|---|
| 5 | 817.0 | 45.00 | 43.47 |

* $x$ represents the carbon content in % by weight of the raw material.
$y$ represents the benzene content in ppm of the pyrolysis products.

EXAMPLE 2

By using the apparatus described in Example 1, the linear relationship between the organic carbon content of sediments of raw rocks and the benzene content of the pyrolysis products of these rocks, is determined by treating the 195 samples described in Example 1, but at another pyrolysis temperature than that of Example 1. These 195 samples are pyrolyzed at a temperature of 900° C, according to the embodiment described in Example 1, and the benzene content of the products of each pyrolysis is determined. According to a known process, the organic carbon content of these samples is determined. The analysis of the results shows the following linear relationship:

$$y = 45.58\ x + 1.35$$

wherein $y$ represents the benzene content expressed in ppm, and $x$ the organic carbon content, expressed in percent by weight.

On the basis of this relationship, the carbon content of any sample of raw material, for instance, raw rock, is very quickly determined.

The embodiment described in part B of Example 1 is repeated to determine the benzene content of the pyrolysis products of six samples of raw rocks which are pyrolyzed at 900° C.

The obtained results are indicated in the hereinbelow Table II.

TABLE II

| Sample | Benzene content (ppm) of the pyrolysis products | Organic carbon content of the raw material according to the relationship $y = 45.58\ x + 1.35$ (*) (% by weight) | Organic carbon content of the raw material according to a known process (% by weight) |
|---|---|---|---|
| 1 | 56.95 | 1.22 | 1.18 |
| 2 | 142.75 | 3.10 | 3.01 |
| 3 | 266.70 | 5.82 | 6.00 |
| 4 | 324.36 | 7.08 | 6.91 |
| 5 | 908.56 | 19.9 | 20.0 |
| 6 | 2,127.76 | 46.65 | 46.70 |

* $x$ represents the carbon content in percent by weight of the raw material.
$y$ represents the benzene content in ppm of the pyrolysis products.

While the invention has now been described in terms of various preferred embodiments, and exemplified with respect thereto, the skilled artisan will readily appreciate that various modifications and changes may be made without departing from the spirit thereof. Accordingly, it is intended that the present invention be limited solely by the scope of the following claims.

What is claimed is:

1. A method for determining the organic carbon content of raw mineral materials, which essentially consists of the steps of:
   (a) determining the relationship between the percent per weight amount of organic carbon content of raw mineral materials and the relative amount of benzene present in the pyrolysis gases which are formed upon pyrolysis of samples of raw mineral materials of known organic carbon content at a pyrolysis temperature of between about 400° and about 1,000° C under an inert gas atmosphere;

(b) pyrolyzing a weighed sample of a crushed raw mineral material of unknown organic carbon content under an inert gas atmosphere at the same temperature as that which is used in the determining step (a), whereby pyrolysis gases are formed;

(c) determining the relative amount of benzene which is present in the pyrolysis gases; and, (d) determining the percent per weight amount of organic carbon content in the crushed raw mineral material which is equivalent to said amount of benzene determined in step (c) from the relationship which has been determined in step (a).

2. The process as defined in claim 1, further comprising the step of sweeping through the pyrolysis zone an inert gas prior to pyrolyzing the sample of the raw mineral material.

3. The process as defined in claim 1, wherein step (c) is carried out chromatographically.

4. The process as defined in claim 3, wherein the pyrolysis gases are carried into a chromatography column by sweeping with an inert gas.

5. The process as defined in claim 2, wherein the inert gas is selected from the group consisting of argon, helium and nitrogen.

6. The process as defined in claim 1, wherein step (c) further comprises the steps of separating the components of the pyrolysis gases in a chromatography column and detecting the benzene component of the pyrolysis gases in a detector.

* * * * *